United States Patent [19]
Selitrennikoff

[11] Patent Number: 4,873,196
[45] Date of Patent: Oct. 10, 1989

[54] PROTOPLASTS OF TEMPERATURE-SENSITIVE STRAINS OF NEUROSPORA CRASSA OS-1

[75] Inventor: Claude P. Selitrennikoff, Golden, Colo.

[73] Assignee: University Patents, Inc., Westport, Conn.

[21] Appl. No.: 771,389

[22] Filed: Aug. 30, 1985

Related U.S. Application Data

[63] Continuation of Ser. No. 382,847, May 27, 1982, abandoned.

[51] Int. Cl.$^4$ .................. C12N 1/14; C12R 1/645
[52] U.S. Cl. ...................... 435/254; 435/911; 935/68
[58] Field of Search .................. 435/254–256, 435/253, 317, 820, 911; 935/68

[56] References Cited

PUBLICATIONS

Hamilton et al., J. Bacter., 88(4): 1084–1086, (1964).
Scarborough et al., Anal. Biochem., 61: 441–447, (1974).
Bachman et al., J. Bacter., 78: 550–556, (1959).
Bigger et al., J. Gen. Microbiol., 71: 159–166, (1972).
Frobisher, *Fundamentals of Microbiology*, 8th Edition, W. B. Saunders Company, 293, (1970).
Selitrennikoff et al., Exp. Mycol., 5: 155–151, (1981).
Selitrennikoff et al., Exp. Mycol., 3: 363–373, (1979).
Emerson et al., Proc. Natl. Acad. Sci., USA, 44: 668–671, (1958).
Selitrennikoff et al., Chemical Abstracts, 96: 159016p, p. 423, (1982).
Bachman (Ed.), Neurospora Newsletter, 22: 15–16, (1975).
Spurr, J. Ultrastructure Res., 26: 31–43, (1969).
Baguley et al., Eur. J. Biochem., 97: 345–351, (1979).
Perez et al., J. Gen. Microbiol., 129: 245–250, (1983).

*Primary Examiner*—Esther M. Kepplinger
*Attorney, Agent, or Firm*—Barbara A. Shimei

[57] ABSTRACT

This invention concerns conditional protoplasts of temperature-sensitive variants of the osmotic-1 mutant strain of *Neurospora crassa*, and method of making same.

14 Claims, 3 Drawing Sheets

PROTOPLASTS OF TEMPERATURE-SENSITIVE STRAINS OF NEUROSPORA CRASSA OS-1

This is a continuation of application Ser. No. 382,847 filed May 27, 1982, now abandoned.

This invention relates to conditional protoplasts derived from temperature-sensitive variants of the osmotic-1 mutant strain of *Neurospora crassa*, and a method of making same. Protoplasts are defined as cells which are limited by morphologically normal plasma membrane and which are devoid of surface-bound cell-wall material; they are therefore ismotically sensitive and do not stain with Calcoflor White M2R New [a fluorescent white optical brightener used as a stain for surface-bound cell-wall material, American Cyanamid Company, Wayne, N.J. See Bachman, B. J., and D. M. Bonner, *J. Bacteriol.* 78: 550-556 (1959); Gull, K., P. M. Moore, and A. P. J. Rince, *Trans. Brit. Mycol. Soc.* 59: 79-85 (1972).] A conditional protoplast is defined as a protoplast whose formation from, and regeneration to, complete (walled) cells is regulated by defined external parameters which may be manipulated to control the presence or absence of surface-bound cell wall.

Conditional protoplasts of *Neurospora crassa* are useful in the detection of anti-fungal compounds which act by exhibiting cell-wall formation. Their lack of surface-bound cell wall also makes these conditional protoplasts ideal eucaryotic hosts in recombinant DNA technology.

Prior art mechanisms for obtaining protoplasts of *Neurospora crassa* involve treatment with cell-wall degrading enzymes, such as may be found in snail gut [see, e.g., Scarborough, G. A., and T. H. Schulte, *Anal. Biochem.* 61: 441-447 (1974); Emerson, S., and M. R. Emerson, Proc. *Nat. Acad. Sci. USA* 44: 669-671 (1958); Bachman, B. J. and D. M. Bonner, J. Bacteriol. 78: 550-556 (1959)]. Such enzymatic treatment tends to damage the cell membranes and also results in a population with a certain percentage of enucleate cells, thus grossly affecting cell viability. It has also been reported that the osmotic-1 strain of *Neurospora crassa* forms crude protoplasts (retaining fragments of surface-bound cell wall) when cultured in medium containing high concentrations of sorbose [Hamilton, J. G., and J. Calvert, *J. Bacteriol* 88: 1084-1086 (1964)]. In addition to the above-described disadvantages, populations of protoplasts formed by either of these two methods are unstable; a variable percentage of the cells will spontaneously regenerate cell-wall over time.

There is a known mutant, the wall-less variant *Neurospora crassa* slime [Bigger, C. H., M. R. White, and H. Braymer, *J. Gen. Microbiol.* 71: 159-166 (1972)], which forms stable protoplasts at temperatures from 23° C. to 37° C. This mutant however is incapable of forming normal cell wall structures and so cannot revert or be induced to form normal whole cells.

It is a purpose of this invention to provide conditional protoplasts of *Neurospora crassa* with intact plasma membranes, essentially devoid of surface-bond cell wall material, which are stable and whose expression or repression of cell wall synthesis can be regulated by simple manipulation of external conditions.

It has now been discovered that osmotic-1 strains of *Neurospora crassa* bearing temperature sensitive alleles [e.g., allele (NM233(t)) or (NM204(t))] will form healthy protoplasts substantially free of surface-bound cell wall material and with intact plasma membranes, when grown in a culture medium containing sorbose and Polyoxin at temperatures above 34° C., and that these protoplasts will remain stable under these conditions. Transfer of these protoplasts to a medium containing sorbitol and incubation at temperatures below 27° C. will result in the regeneration of whole cells bearing morphologically normal cell wall. The production of protoplasts and the regeneration of whole cells from these protoplasts can thus be controlled at will.

A better understanding of the invention can be had by reference to the accompanying figures, wherein.

Figure 1:
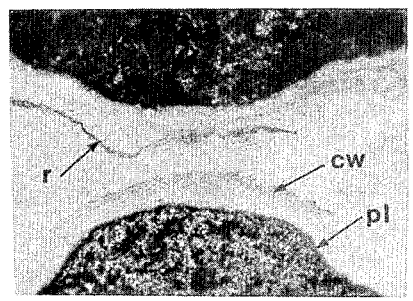
FIG. 1 shows a section of macroconidia of *Neurospora crassa* osmotic-1 [os-1 (NM 233(t))]; Nicotinic acid-1 (nic-1 (S1413)), a, grown at 25° C. on Vogel's N Minimal Medium plus 10 μg/ml nicotinamide plus 1.5% agar (31,100 X). [r=rodelet layer, cw=cell wall, pl=plasma membrane].
Figure 3:
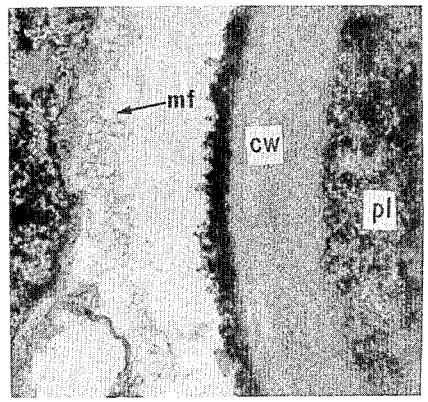
FIG. 3 shows a section of regenerated *Neurospora crassa* osmotic-1 [os-1 (NM 233(t))]; nicotinic acid-1 (nic-1 (S1413)), a, formed from protoplasts produced according to Example 2 and transferred to Nelson's Medium B supplemented with 10 μg/ml nicotinamide, followed by incubation at 25° C. (100,000 X) [cw=cell wall, pl=plasma membrane, mf=microfibril].
Figure 2A:
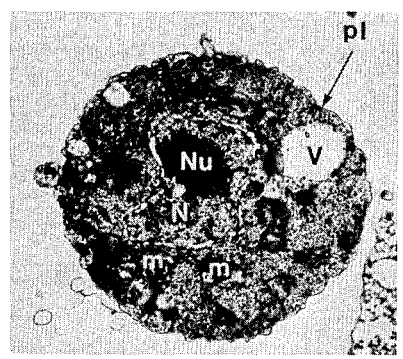
FIG. 2 shows sections of protoplasts of *Neurospora crassa* osmotic-1 [os-1 (NM 233(t))]; nicotinic acid-1 (nic-1 (S1413)), a, grown at 37° C. in Nelson's Medium A supplemented with 10 μg/ml nicotinamide and 200 μg/ml Polyoxin B (A=12,900 X; B=29,900 X) [Nu=nucleolus, v=vesicle, pl=plasma membrane, N=nucleus, m=mitochondrion].
Figure 2B:
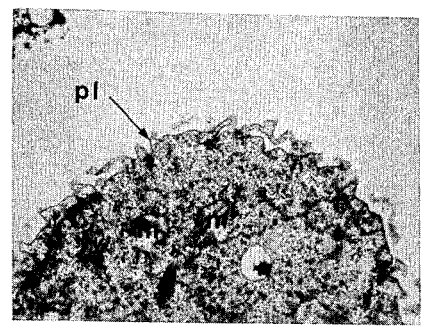

There are six known gene mutations of *Neurospora crassa* which result in an osmotic phenotype (defined as sensitivity to the presence of 4% sodium chloride); of these only the alleles NM 233(t) and NM 204(t) of the gene designated as osmotic-1 (also known as os-1) are temperature sensitive. None of the six known osmotic phenotypes of *Neurospora crassa* spontaneously form protoplasts, and it has now been discovered that only the osmotic-1 mutant will form protoplasts when treated according to the process of the present invention, and further that only those variants of *Neurospora crassa* os-1 bearing one of the temperature sensitive alleles will regenerate cell walls under permissive conditions. Accordingly, the present invention concerns conditional protoplasts derived from temperature-sensitive osmotic-1 variants of *Neurospora crassa*.

*Neurospora crassa* os-1 (NM 233(t)) and os-1 (NM 204(t)) are temperature-sensitive osmotic strains; growth and morphology are wild type at permissive temperatures (22°-27° C.) whereas at non-permissive temperatures (34°-39° C.) the morphology undergoes certain well-characterized changes [Selitrennikoff, C. P., S. Slemmer, and R. E. Nelson, *Exp. Micol.* 3: 363-373 (1979)]. These strains are on permanent deposit at the Fungal Genetic Stock Center, University of Kansas Medical Center, Kansas City, Kans. 66103 and are freely available under their accession numbers:

1287 *Neurospora crassa* os-1 (NM 233(t)),A, ATCC 20885

1200 *Neurospora crassa* os-1 (NM 233(t)),a ATCC 20884

1637 *Neurospora crassa* os-1 (NM 204(t)),A ATCC 20887

2273 *Neurospora crassa* os-1 (NM 204(t)),a ATCC 20886

The designation A or a refers to mating types known to those skilled in the art and is irrelevant to the purposes of this invention.)

It is to be understood that the present invention is not limited to protoplasts of *Neurospora crassa* os-1 [NM 233(t)] or os-1 [NM 204(t)], which are given for illustrative purposes only. The present invention includes all osmotic-1 strains of *Neurospora crassa* which are temperature sensitive and which form conditional protoplasts when treated by the process of the present invention.

It is also to be understood that the temperature sensitive osmotic-1 strains of *Neurospora crassa* used to produce the protoplast of the present invention may have additional genetic characteristics such as, e.g., antibiotic sensitivity or resistance or auxotrophic characteristics, which distinguish said organisms from *Neurospora crassa* wild type. The present invention includes protoplasts created from all strains of *Neurospora crassa* bearing the temperature-sensitive osmotic-1 alleles, with or without such additional non-wild type phenotypic characteristics.

The protoplasts of the present invention are made by the following procedure:

A temperature-sensitive variant of *Neurospora crassa* os-1 is grown on agar slants to provide an inoculum. The medium is any suitable *Neurospora crassa* medium known to those skilled in the art, e.g. Vogel's N Minimal Medium [Vogel, H. J., *Neurospora. Microbiol. Genet. Bull.* 13: 42 (1956)], which comprises Vogel's salts plus 1.5% (w/v) sucrose as a carbon source:

| VOGEL'S SALTS | |
|---|---|
| Sodium citrate | 3 g |
| $KH_2PO_4$ | 5 g |
| $NH_4NO_3$ | 2 g |
| $MgSO_4.7H_2O$ | 0.2 g |
| $CaCl_2.2H_2O$ | 0.1 g |
| Biotin | 250 µg |
| citric acid.$H_2O$ | 5 mg |
| $ZnSO_4.7H_2O$ | 5 mg |
| $Fe(NH_4)_2(SO_4)_2.6H_2O$ | 1 mg |
| $CuSO_4.5H_2O$ | 250 µg |
| $MnSO_4.1H_2O$ | 50 µg |
| $H_3BO_3$ | 50 µg |
| $Na_2MoO_4.2H_2O$ | 50 µg |
| $H_2O$ to | 1000 ml |

To this medium is added 1.5% (w/v) agar. The slant is inoculated with a culture of temperature-sensitive *Neurospora crassa* os-1 and incubated at about 22°–37° C., preferably at about 25° C., until the cells have matured and developed conidia.

Liquid cultures are prepared by inoculating washings of spores from agar slants into "protoplast meduim", which is defined as a suitable *Neurospora crassa* growth medium supplemented with about 7.5–12.5% (w/v) (preferably about 10%) sorbose or an equivalent amount of a $\beta(1\rightarrow 3)$ glucan synthesis inhibitor, and about 200–1000 µg/ml (preferably about 400 µg/ml) Polyoxin [a class of peptidyl-pyrimidine nucleoside antibiotics produced by *Streptomyces cacaoi* var. *asoensis*, Kaken Chemical Company, Ltd., Tokyo, Japan]. Polyoxin B and D are preferred; particularly preferred is Polyoxin B. The protoplast medium must also be osmotically balanced to prevent osmotic shock to the protoplasts as they develop. An example of a suitable protoplast medium is Nelson's Medium A (Vogel's salts ( as described above) plus 10% (w/v) sorbose plus 2% (w/v) sucrose as a carbon source) [Nelson, R. E., B. Littlewood, and R. L. Metzenberg, *Neurospora Newslett.* 22: 15–16 (1975)]; this medium is then supplemented with about 400 µg/ml Polyoxin B. The sorbose functions both as a $\beta(1\rightarrow 3)$ glucan synthesis inhibitor and as a buffer against osmotic shock.

The liquid protoplast medium is inoculated by first washing a slant with a small volume of the same medium. If desired, this washing may be done without the supplementation by Polyoxin. The washed spores are suspended and filtered to remove debris and fungal aggregates and are inoculated into the liquid protoplast medium at an initial concentration of about $1-10\times 10^5$ cells/ml. The culture is aerated and incubated at a nonpermissive temperature (about 37°–40° C.) for about 20–28 hours, preferably for about 24 hours at about 37° C., to yield the desired protoplasts.

If desired, the culture may be selectively enriched for high protoplast yield by the following procedure:

A culture of protoplasts prepared as above is filtered into fresh sterile protoplast medium at a concentration of $1-5\times 10^6$ cells/ml and incubated as above. The culture is grown and filtered in this manner for a total of 7 days, at which time a pure culture of protoplasts has been achieved.

The protoplasts are stable when continuously propagated in fresh protoplast medium at a non-permissive temperature, for periods up to 35 days. The protoplasts may also be frozen and stored for future use.

Whole cells are regenerated when desired by transfer to an osmotically supportive medium at 22°–25° C., preferably at 25° C. The medium may be any suitable *Neurospora crassa* growth medium supplemented with about 7–10% (w/v) (preferably about 7.5%) sorbitol. Alternatively, an equivalent amount of any suitable inorganic ion to provide the same osmotic balance may be used, e.g. 0.4M $MgSO_4$. An example of a suitable medium is Nelson's Medium B (Vogel's salts (as described above) plus 7.5% (w/v) sorbitol plus 1.5% (w/v) sucrose as a carbon source) [Nelson et. al., supra]. The cells are incubated in this medium for about 20–28 hours, preferably about 24 hours, at which time >90% of the protoplasts will have regenerated normal cell wall.

A further understanding of this invention may be had from the following non-limiting examples. Unless otherwise specified, all procedures were performed at room temperature (approximately 22° C.) and at 1 atm. pressure.

EXAMPLE 1

Inoculum

Conidia from a stock of *Neurospora crassa* Shear et Dodge, osmotic-1 [os-1(NM 233(t))]; nicotinic acid-1 (nic-1 (S1413)), a, were inoculated onto 5 ml. slants of Vogel's N Minimal Medium plus 1.5% agar, supplemented with 10 µg/ml nicotinamide. The cultures were then incubated at 25° C. for 6 days in ambient light to produce mature macroconidia.

A sample of macroconidia grown as described above were washed from a slant with 5 mls. Nelson's Medium A supplemented with 10 µg/ml nicotinamide, and harvested by centrifugation at 2° C. for 5 min. at 2000Xg. The cell pellet was resuspended in ice-cold Vogel's N Minimal Medium supplemented with 10 µg/ml nicotinamide and containing 3% (v/v) glutaraldehyde; the sample was then processed for transmission electron microscopy as described in Selitrennikoff et al., supra, except that Spur's resin [Spur, A. P., *J. Ultrastruct Res.* 26: 31–43 (1969)] was substituted for Luft's Epon resin. The resultant processed macroconidia were photographed on a Philips 300 electron microscope at 60 KeV to yield Figure I, which is representative of temperature-sensitive variants of *Neurospora crassa* os-1 grown under permissive conditions.

EXAMPLE 2

Formation of Protoplasts

Macroconidia of *Neurospora crassa* osmotic-1 [os-1 (NM 233(t))]; nicotinic acid-1 (nic-1 (S1413)), a, prepared as in Example 1 were washed from an agar slant with a small amount of sterile Nelson's Medium A, sterile filtered through cotton, and inoculated into 50 mls. sterile Nelson's Medium A supplemented with 10 μg/ml nicotinamide and 200 μg/ml Polyoxin B, in a sterile 250 ml. flask. The cells were incubated at 37° C. for 24 hours on a New Brunswick G76 orbital shaker (140 RPM). A small aliquot was then harvested by centrifugation at 500Xg at 25° C. and the pellet examined microscopically. The cells were a mixture of protoplasts and wall-bounded cells.

The remaining culture was sterile filtered through glass wool into a clean sterile flask, and the filtrate containing primarily protoplasts was diluted to a concentration of $1 \times 10^6$ organisms/ml with sterile Nelson's Medium A supplemented with 10 μg/ml nicotinamide and 200 μg/ml Polyoxin B. The cells were again incubated for 24 hours at 37° C. with shaking. The above procedure was repeated until the cells had been grown and filtered for a total of 7 days, at the end of which time the culture was comprised exclusively of protoplasts.

A sample of protoplasts prepared as above were harvested by centrifugation at 25° C. for 5 min. at 500Xg, resuspended in ice-cold Nelson's Medium A supplemented with 10 μg/ml nicotinamide and 200 μg/ml Polyoxin B and containing 3% (v/v) glutaraldehye, and processed by electron microscopy as described in Example 1. The result is shown in Figure II, which is representative of protoplasts of temperature-sensitive variants of *Neurospora crassa* os-1 prepared by the process of the present invention.

EXAMPLE 3

Regeneration of Whole Cells

Protoplasts of *Neurospora crassa* osmotic-1 [os-1 (MN 233(t))]; nicotinic acid-1 (nic-1 (S 1413)), a, prepared as in Example 2, were harvested by centrifugation at 500Xg at 25° C. for 5 min., resuspended in 1 ml. of Nelson's Medium B, and diluted to a concentration of $1 \times 10^5$ protoplasts/ml with sterile Nelson's Medium B supplemented with 10 μg/ml nicotinamide. The culture was incubated for 24 hours at 25° C. on a New Brunswick G76 orbital shaker (140 RPM), to yield whole cells with regenerated cell walls which were morphologically normal.

A sample of regenerated cells prepared as above were havested by centrifugation at 25° C. for 5 min. at 500Xg, resuspended in ice-cold Nelson's Medium B supplemented with 10 μg/ml nicotinamide and containing 3% (v/v) glutaraldehyde, and processed for electron microscopy as described in Example 1. The result is shown in Figure III, which is representative of cells of temperature-sensitive variants of *Neurospora crassa* os-1 which have been regenerated from protoplasts of the present invention under permissive conditions in an osmotically balanced medium.

I claim:

1. A temperature-sensitive protoplast of a temperature-sensitive variant of *Neurospora crassa* os-1, characterized in that said protoplast will propagate as protoplasts when grown in a suitable culture medium containing sorbose and Polyoxin at non-permissive temperatures, but transfer of these protoplasts to a medium containing sorbitol and incubation at permissive temperatures will result in the regeneration of whole cells bearing morphologically normal cell wall.

2. The protoplast of claim 1 wherein said temperature-sensitive variant of *Neurospora crassa* os-1 contains the (NM 233(t)) allele.

3. The protoplast of claim 1 wherein said temperature-sensitive variant of *Neurospora crassa* os-1 contains the (NM 204(t)) allele.

4. A process for the production of the protoplast of claim 1, said process comprising inoculating conidia of a temperature-sensitive variant of *Neurospora crassa* os-1 into a suitable osmotically balanced *Neurospora crassa* growth medium supplemented with about 200–1000 μg/ml Polyoxin and a sufficient amount of a $\beta(1\rightarrow3)$ glucan synthesis inhibitor to inhibit the formation of surface-bound cell wall material, at an initial concentration of about $1-10 \times 10^5$ cells/ml, and incubating at a non-permissive temperature with aeration until the cells are converted to protoplasts.

5. The process of claim 4 wherein said suitable osmotically balanced *Neurospora crassa* growth medium is supplemented with about 10% sorbose and about 400 μg/ml of a Polyoxin selected from the group consisting of Polyoxin B and Polyoxin D.

6. The process of claim 4 wherein said temperature-sensitive variant of *Neurospora crassa* os-1 contains the (NM 233(t)) allele.

7. The process of claim 4 wherein said temperature-sensitive variant of *Neurospora crassa* os-1 contains the (NM 204(t)) allele.

8. The process of claim 6 or 7 wherein said non-permissive temperature is about 37° C.

9. The process of claim 4 wherein conidia of a temperature-sensitive variant of *Neurospora crassa* os-1 containing an allele selected from the group consisting of (NM 233(t)) and (NM 204(t)) are inoculated into Nelson's Medium A supplemented with about 400 μg/ml Polyoxin B at an initial concentration of about $1-10 \times 10^5$ cells/ml and incubated at about 37° C. for about 24 hours with aeration.

10. The protoplast of claim 2 wherein said temperature-sensitive variant of *Neurospora crassa* os-1 is *Neurospora crassa* os-1 (NM 233(t)), ATCC 20885 or ATCC 20884.

11. The protoplast of claim 3 wherein said temperature-sensitive variant of *Neurospora crassa* os-1 is *Neurospora crassa* os-1 (NM 204(t)), ATCC 20887 or ATCC 20886.

12. The process of claim 6 wherein said temperature-sensitive variant of *Neurospora crassa* os-1 is *Neurospora crassa* os-1 (NM 233(t)), ATCC 20885 or ATCC 20884.

13. The process of claim 7 wherein said temperature-sensitive variant of *Neurospora crassa* os-1 is *Neurospora crassa* os-1 (NM 204(t)), ATCC 20887 or ATCC 20886.

14. The process of claim 9 wherein said temperature-sensitive variant of *Neurospora crassa* os-1 is selected from the group consisting of ATCC 20884, ATCC 20885, ATCC 20886 and ATCC 20887.

* * * * *

UNITED STATES PATENT AND TRADEMARK OFFICE
CERTIFICATE OF CORRECTION

PATENT NO. : 4,873,196

DATED : October 10, 1989

INVENTOR(S) : Claude P. Selitrennikoff

It is certified that error appears in the above-identified patent and that said Letters Patent is hereby corrected as shown below:

ON TITLE PAGE:

Assignee: Delete "University Patents, Inc., Westport, Conn." and insert --The University of Colorado Foundation, Inc., Boulder, Colorado-- in lieu thereof.

Column 1, after the title and before "This is a continuation ...", insert the following paragraph:

--Research leading to the making of this invention was supported, at least in part, by federal funding. Accordingly, the United States government has certain statutory rights to the invention described and claimed herein.--

Signed and Sealed this

Nineteenth Day of November, 1991

Attest:

HARRY F. MANBECK, JR.

Attesting Officer

Commissioner of Patents and Trademarks